(12) United States Patent
Agouridas et al.

(10) Patent No.: US 6,352,983 B1
(45) Date of Patent: Mar. 5, 2002

(54) 2-HALOGENATED DERIVATIVES OF 5-0 DESOSAMINYL-ERYTHRONOLIDE A, THEIR PREPARATION PROCESS AND THEIR ANTIBIOTIC USE

(75) Inventors: Constantin Agouridas, Nogent sur Marne; Francois Bretin, Ozoir la Ferriere; Alexis Denis; Claude Fromentin, both of Paris, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/416,022

(22) Filed: Oct. 8, 1999

(30) Foreign Application Priority Data

Oct. 15, 1998 (FR) .............................. 98 12937

(51) Int. Cl.$^7$ ...................... A61K 31/55; A61K 31/42; C07D 243/00; C07D 498/00; A61P 31/04
(52) U.S. Cl. .................. 514/220; 514/375; 540/556; 548/218
(58) Field of Search ................. 540/556; 548/218; 514/220, 375

(56) References Cited

U.S. PATENT DOCUMENTS 6,124,269 A * 9/2000 Phan et al. .............. 514/29

FOREIGN PATENT DOCUMENTS

| EP | 0487411 | 5/1992 |
| FR | 2742757 | 6/1997 |
| WO | 9921871 | 5/1999 |

* cited by examiner

*Primary Examiner*—Brenda Coleman
(74) *Attorney, Agent, or Firm*—Bierman, Muserlian and Lucas

(57) ABSTRACT

Novel compounds of the formula

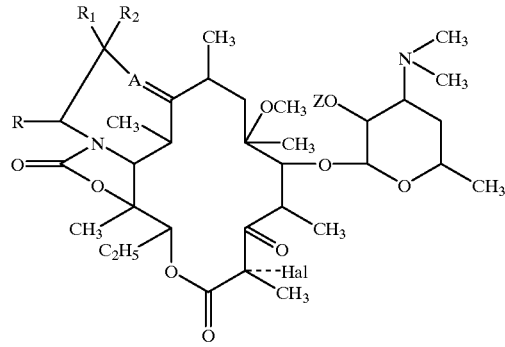

wherein the substituents are defined as in the application having antibiotic properties.

12 Claims, No Drawings

2-HALOGENATED DERIVATIVES OF 5-0 DESOSAMINYL-ERYTHRONOLIDE A, THEIR PREPARATION PROCESS AND THEIR ANTIBIOTIC USE

SUMMARY OF THE INVENTION

Novel 2-halogenated derivatives of 5-0-desosaminyl-erythronolide A and their use.

OBJECTS OF THE INVENTION

It is an object of the invention to provide the novel compounds of formula I and their acid addition salts and a process for their preparation.

It is another object of the invention to provide novel antibiotic compositions and a method of treating bacterial infections in warm-blooded animals.

These and other objects and advantages of the invention will become obvious from the following detailed description.

THE INVENTION

The novel products of the invention are compounds selected from the group consisting of a compound of the formula

I wherein A is nitrogen or N→O, $R_1$ and $R_2$ are individually selected from the group consisting of hydrogen and alkyl of 1 to 18 carbon atoms, R is selected from the group consisting of hydrogen and —$(CH_2)_m$OB, Hal is halogen, m and n are individually an integer from 1 to 8, B is hydrogen or —C(=O)—Ar or —$(CH_2)_n$—Ar, Ar is a mono- or polycyclic aryl or heteroaryl, Z is hydrogen or acyl of an organic carboxylic acid of up to 18 carbon atoms and its non-toxic, pharmaceutically acceptable acid addition salts.

Examples of acids for the acid addition salts are acetic acid, propionic acid, trifluoroacetic acid, maleic acid, tartaric acid, methanesulfonic acid, benzenesulfonic acid, p-toluenesulfonic acid and particularly stearic acid, ethyl-succinic acid or laurylsulfonic acid.

Examples of alkyl are methyl, ethyl, propyl, isopropyl, n-butyl, isobutyl, terbutyl, decyl and dodecyl.

Examples of aryl are phenyl or naphthyl and examples of heteroaryl are thienyl, furyl, pyrolyl, thiazolyl, oxazolyl, imidazolyl, thiadiazolyl, pyrazolyl or isopyrazolyl, pyridyl, pyrimidyl, pyridazinyl and pyrazinyl and also indolyl, benzofurannyl, benzothiazyl and quinolinyl.

Examples of substituents are at least one of hydroxyl, halogen, —$NO_2$, —C≡N, alkyl, alkenyl or alkynyl, O-alkyl, O-alkenyl or O-alkynyl, S-alkyl, S-alkenyl or S-alkynyl and N-alkyl, N-alkenyl or N-alkynyl of up to 12 carbon atoms optionally substituted by at least one halogen, —N($R_a$)($R_b$)

$R_a$ and $R_b$ individually being hydrogen or alkyl of up to 12 carbon atoms,

—C(=O)—$R_3$ $R_3$ being alkyl of up to 12 carbon atoms, or an optionally substituted aryl or heteroaryl radical, carbocyclic aryl, O-aryl or S-aryl, or heterocyclic aryl, O-aryl or S-aryl with 5 or 6 members comprising at least one heteroatom, optionally substituted by one or more of the above substituents.

Hal is halogen, preferably fluorine or chlorine. When one of the substituents is halogen, it is preferably fluorine, chlorine or bromine.

Among the preferred compounds of formula I are those wherein $R_1$ and $R_2$ are hydrogen, those wherein A is nitrogen, those wherein Hal is fluorine, those wherein R is hydrogen and those wherein R is —$CH_2OH$.

The process for the preparation of a compound of formula I comprises reacting a compound of the formula

II wherein Hal is halogen and OM is a protected hydroxyl with a compound of the formula $H_2N$—CH($(CH_2)_mOH$)—$CH_2$—NH—$CH_2$—$C_6H_5$ wherein m is an integer from 1 to 8 to obtain a compound of the formula

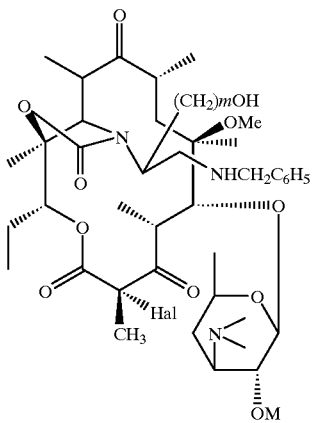

deprotecting the 2'-hydroxyl to obtain a compound of the formula

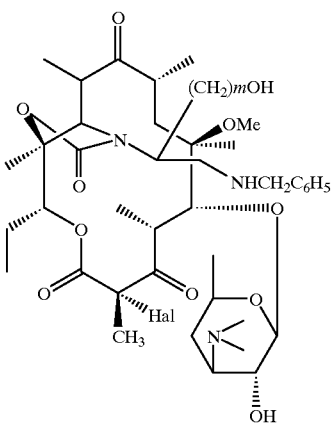

reacting the latter with a debenzylating agent to obtain a compound of the formula

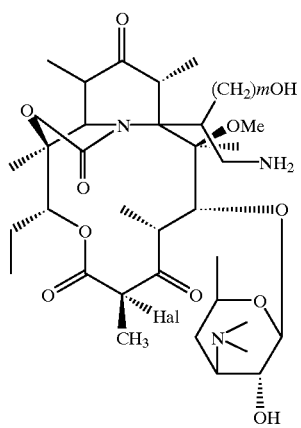

reacting the latter with a cyclization agent to form a compound of the formula

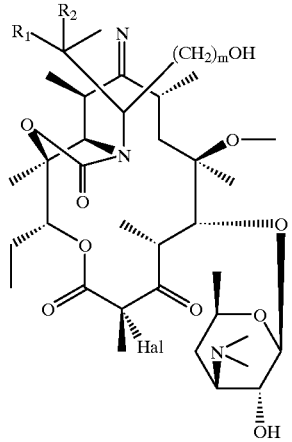

wherein R is —(CH$_2$)$_m$—OH and optionally subjecting the latter to aralkylating or acylating agent to obtain a compound of claim 1 wherein B is —(CH$_2$)$_n$—Ar or

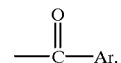

The starting compounds of formula II are described in French patent application 98-04366 filed Apr. 8, 1998 and a detailed description of the process for the preparation of compounds of formula II wherein Hal is fluorine is described herein.

The process comprises reacting a compound of the formula

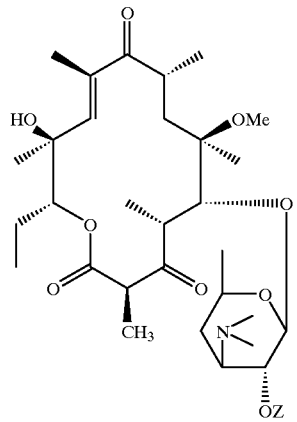

wherein —OZ is —OH or a protected hydroxyl with a fluorination agent to obtain a compound of the formula

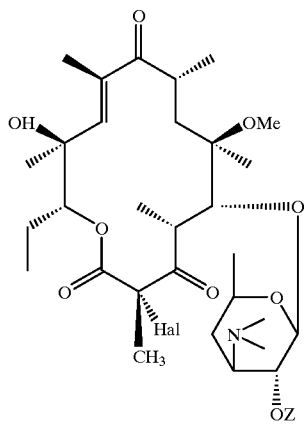

which is then reacted with carboxyldiimidazole to obtain the compound of formula II. Other products can be prepared in an analogous manner.

Preferably, OZ is acetyl or benzoyl and the protected hydroxyl can be released by methanolysis. The debenzylation may be effected by hydrogenation such as with palladium on carbon in the presence of ammonium formate at methanol reflux and cyclization may be effected at ethanol reflux in the presence of acetic acid. The acylation or arylation can be carried out by standard procedures.

The compound S of formulae IV, V and VI are novel and are part of the invention.

In a variation of the process to prepare the compounds of formula I, a compound of the formula

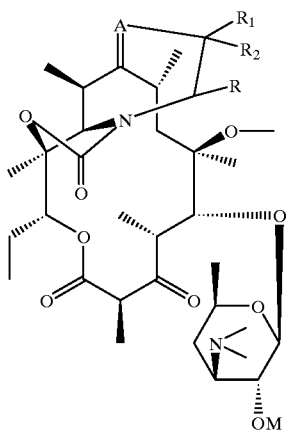

(IIIA)

wherein A, R, $R_1$ and $R_2$ are defined as above and —OM is a protected hydroxyl is reacted with a halogenation agent to obtain a compound of the formula

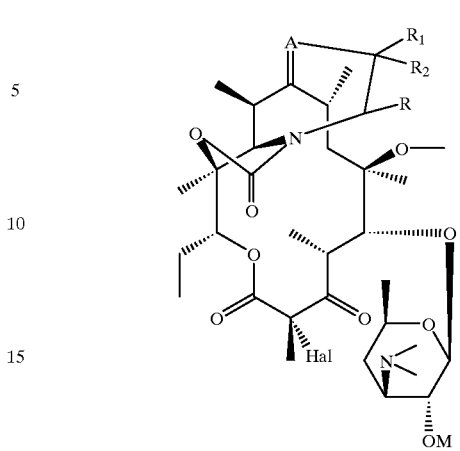

which is optionally reacted with an agent to free the 2'-hydroxyl to obtain the compound of formula I wherein in Z is hydrogen and optionally with an esterification agent to obtain the 2'-acylated compound or with an acid to form the acid addition salt.

The preferred halogenation agent is bisphenyl sulfonylimide of the Formula

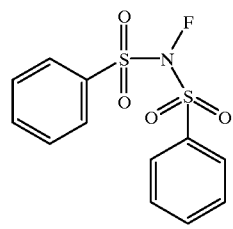

The novel antibiotic compositions of the invention are comprised of an antibiotically effective amount of a compound of formula I and its non-toxic, pharmaceutically acceptable acid addition salts and an inert pharmaceutical carrier. The compositions may be in the form of plain or sugar-coated tablets, gelatin capsules, granules, suppositories, injectable preparations, ointments, creams, gels.

Examples of the pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions can also be present in the form of a powder intended to be dissolved extemporaneously in an appropriate vehicle, for example, apyrogenic sterile water.

The compositions have a very good antibiotic activity on gram ⊕ bacteria such as staphylococcis, streptococcis, pneumococcis and therefore are useful in the treatment of germ-sensitive infections and particularly in that of staphylococcia such as staphylococcal septicaemias, malignant staphylococcia of the face or skin, pyodermitis, septic or suppurant wounds, boils, anthrax, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as pneumonia, bronchitis; brucellosis, diphtheria, gonococcal infection.

The compositions are also active against infections caused by germs such as Haemophilus influenzae, Rickettsia, Mycoplasma pneumoniae, Chlamydia, Legionella, Ureaplasma, Toxoplasma, or germs of the Mycobacterium genus.

The method of treating bacterial infections in warm-blooded animals comprises administering to a warm-blooded animal an antibiotically effective amount of a compound of formula I or its acid addition salt. The compounds can be administered buccally, rectally, parenterally or by topical application on the skin and mucous membranes, but the preferred administration route is the buccal route. The usual effective daily dose is 2 to 15 mg/kg depending on the method of administration and the active compound.

In the following examples, there are described various preferred embodiments to illustrate the invention. However, it is to be understood that the invention is not intended to be limited to the specific embodiments.

EXAMPLE 1

[3as-(3aR*,4S*,7R*,9S*,10S*,11S*,13S*,15S*, 15aS)*]-4-ethyl-7-fluoro-3a,4,10,11,12,13,15,15a-octahydro-11-methoxy-3a,7,9,11,13,15-hexamethyl-10-[[3,4,6-trideoxy-3-(dimethyl-amino)-.beta.-D-xylo-hexopyranosyl]oxy]-14,1-(nitriloethano)-2H-oxacyclotetradecino[4,3-d]oxazole-2,6,8(9H)-trione Stage A: [3aS-(3aR*,4S*,7S*,9S*,10S*,11S*,13S*,15S*, 15aS*)]-4-ethyl-3a,4,10,11,12,13,15,15a-octahydro-11-methoxy-3a,7,9,11,13,15-hexamethyl-10-[[3,4,6-trideoxy-3-(dimethyl-amino)-2-0-(trimethylsilyl)-.beta.-D-xylo-hexopyranosyl]oxy]-14,1-(nitriloethano)-2H-oxacyclotetradecino[4,3-oxazole-2,6,8(7H, 9H)-trione A mixture of 0.9835 g of [3aS-(3aR*,4S*,7S*,9S*,10S*, 11S*,13S*,15S*,15aS*)]-4-ethyl-3a,4,10,11,12,13,15,15a-octahydro-11-methoxy-3a,7,9,11,13,15-hexamethyl-10-[[3, 4,6-trideoxy-3-(dimethyl-amino)-.beta. -D-xylo-hexopyranosyl]oxy]-14,1-(nitriloethano)-2H-oxacyclotetradecino [4,3-d]oxazole-2,6,8(7H,9H)-trione (EP 0638585) and 9.8 ml of THF were stirred for 5 minutes and then 105 mg of imidazole and 0.327 ml of hexamethylsilylamine [(CH₃)₃Si]₂NH were added. The mixture was stirred for 5 days during which twice 0.2 eq of 3-pyrazolamine and twice 0.2 eq of hexamethylsilylamine were added followed by drying and taking up in methylene chloride. 30 ml of a solution of sodium dihydrogen phosphate were added and the mixture was stirred for 15 minutes followed by decanting. The aqueous phase was extracted with methylene chloride and the chloromethylenic phases were combined, dried, filtered and evaporated to obtain 1.2259 g of the desired product.

Stage B: [3aS-(3aR*,4S*,7S*,9S*,10S*,11S*,13S*,15S*, 15aS*)]-4-ethyl-7-fluoro-3a,4,10,11,12,13,15,15a-octahydro-11-methoxy-3a,7,9,11,13,15-hexamethyl-10-[[3,4,6-trideoxy-3-(dimethylamino)-2-0-(trimethylsilyl)-.beta.-D-xylo-hexopyranosyl]oxy]-14,1-(nitriloethano)-2H-oxacyclotetra-decino[4,3-d]oxazole-2,6,8(7H,9H)-trione A solution of 1.1003 g of the product of Stage A and 11 ml of THF was cooled to –10° C. and 1.86 ml of potassium terbutylate in THF were added. The mixture was stirred for 5 minutes and 0.588 g of

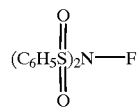

were added. The mixture was stirred for 10 minutes at –10° C. and the reaction medium was allowed to return to ambient temperature. The mixture was stirred at ambient temperature for 1 hour 30 minutes followed by filtration. The precipitate was rinsed with ethyl acetate and the filtrate was concentrated and taken up to 10 ml of ethyl acetate, 10 ml of water and 5 ml of a 20% aqueous solution of ammonium hydroxide. The mixture was stirred for 10 minutes followed by decanting, washing with water and extracting with ethyl acetate. The organic phases were combined, dried, filtered and evaporated to dryness to obtain 1.1067 g of the desired product.

Stage C: [3aS-(3aR*,4S*,7S*,9S*,10S*,11S*,13S*,15S*, 15aS*)]-4-ethyl-7-fluoro-3a,4,10,11,12,13,15,15a-octahydro-11-methoxy-3a,7,9,11,13,15-hexamethyl-10-[[3,4,6-trideoxy-3-(dimethylamino)-.beta.-D-xylo-hexopyranosyl]oxy]-14,1-(nitriloethano)-2H-oxacyclotetradecino[4,3-d]oxazole-2,6,8(9H)-trione 1.13 ml of a solution of tetrabutylammonium fluoride in THF were added to a solution of 0.55 g of the product of Stage A and 5.5 ml of THF and the mixture was stirred for 4 hours 30 minutes. The solvent was evaporated off and the residue was taken up in 5 ml of ethyl acetate, 5 ml of water and 2 ml of a 20% solution of ammonium hydroxide. The mixture was stirred for 15 minutes followed by decanting. The aqueous phase was extracted with ethyl acetate followed by washing with water. The aqueous phase was re-extracted and the organic phases were combined, dried, filtered and evaporated to dryness to obtain 0.4134 g of the desired product.

EXAMPLE 2

(3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-.beta.-D-xylo-hexopyranosyl]oxy]-14,1-(nitriloethano)-2H-oxacyclotetradecino[4,3-d] oxazole-2,6,8(7H, 9H)-trione State A: 11,12-dideoxy-3-de[[(2,6-dideoxy-3-C-methyl-3-0-methyl-.alpha.-L-ribo-hexopyranosyl)oxy]-2-fluoro-6-0-methyl-3-oxo-12,11-[oxycarbonyl[[(2R)-1-hydroxy-3-[(phenylmethyl)amino]-2-propyl]imino]-2'-acetoxy 6.7 g of the product of Preparation I were introduced into a solution of 8.33 g of (R)-2-amino-3-[(phenyl-methyl) amino]-1-propanol, 67 ml of acetonitrile and 6.7 ml of water and after the is reaction mixture was taken to 55°, it was maintained at this temperature for 21 hours. The reaction mixture was then poured into a water-ethyl acetate mixture followed by decanting, extracting with ethyl acetate, drying, filtering and evaporating to obtain 10.7 g of the desired product.

Stage B: 11,12-dideoxy-3-de[[(2,6-dideoxy-3-C-methyl-3-0-methyl-.alpha.-L-ribo-hexopyranosyl)oxy]-2-fluoro-6-0-methyl-3-oxo-12,11-[oxycarbonyl[[(2R)-1-hydroxy-3-[(phenylmethyl)amino]-2-propyl]imino]-erythromycin 107 ml of methanol were added to 10.7 g of the product of Stage A and the mixture was stirred for 15 hours at ambient temperature. The methanol was evaporated off followed by drying to obtain 9.47 g of crude sought product which was purified by 2 successive chromatographies eluting with a methylene chloride/methanol/ammonium hydroxide mixture (96-4-0.4), then eluting with an ethyl acetate/triethylamine mixture to obtain 2.66 g of the desired product.

Stage C: 11,12-dideoxy-3-de[(2,6-dideoxy-3-C-methyl-3-0-methyl-.alpha.-L-ribo-hexopyranosyl)oxy]-2-fluoro-6-0-methyl-3-oxo-12,11-[oxycarbonyl[((2R)-1-amino-3-hydroxy-2-propyl)imino]]-erythromycin 0.8 g of the product of Stage B, 8 ml of methanol, 315 mg of ammonium formate and 800 mg of palladium on carbon were mixed together and the reaction mixture was refluxed for 4 hours and 30 minutes under hydrogen. The reaction medium was allowed to return to ambient temperature and then was filtered. The filtrate was concentrated under reduced pressure to obtain 660 mg of product which was taken up in 20 ml of ethyl acetate followed by pouring into a 20% solution of ammonium hydroxide. The mixture was stirred followed by decanting and extracting with ethyl acetate, drying and filtering to obtain 660 mg of the desired product.

Stage D: 3aS,4R,7S,9R,10R,11R,13R,15R,15aR,18S)-4-ethyl-7-fluoro-3a,4,10,11,12,13,15,15a-octahydro-18-hydroxymethyl)-11-methoxy-3a,7,9,11,13-15-hexamethyl-10-[[3,4,6-tridsexy-3-(dimethylamino)-.beta.-D-xylo-hexopyranosyl]oxy]-14,1-(nitriloethano)-2H-oxacyclotetradecino[4,3-d]oxazole-2,6,8(7H,9H)-trione 0.3795 g of the product of Stage C, 4 ml of ethanol and 62 μl of acetic acid were refluxed with stirring for 6 days and then was allowed to return to ambient temperature, followed by concentrating under reduced pressure. The residue was taken up in ethyl acetate and the solution was poured into a 20% solution of ammonium hydroxide. The mixture was stirred for 15 minutes followed by decanting, extracting with ethyl acetate, drying, filtering, rinsing and evaporating to obtain 0.304 g of product which was purified by chromatography on silica eluting with a chloroform/isopropanol/ammonium hydroxide mixture (90-10-0.4) to obtain 88 mg of the desired product.

Preparation 1

12-(oxycarbonylimidazol)-11-deoxy-10,11-didehydro-3-de[-2,6-dideoxy-3-C-methyl-3-0-methyl-α-L-ribohexopyranosyl)oxy]6-0-methyl-3-oxo-erythromycin 2'-acetoxy 2α-fluoro Stage A: 11-deoxy 10,11-dedehydro-3-de[(2,6-dideoxy 3-0-methyl α-L-ribohexopyranosyl)oxy]6-0-methyl 3-oxo erythromycin.

A mixture of 8.722 g of 11-deoxy-10,11-didehydro-3-de[(2,6-dideoxy-3-0-methyl-α-L-ribohexopyranosyl)-oxy]-6-0-methyl-3-oxo-erythromycin (EP 596802) 2'-acetate and 350 ml of anhydrous methanol was stirred for 44 hours. The reaction medium was evaporated, taken up with methylene chloride and dried to obtain 8.794 g of the desired product.

Stage B: 11-deoxy-10,11-didehydro-3-de[(2,6-dideoxy-3-0-methyl-α-L-ribohexopyranosyl)-oxy]-6-0-methyl-3-oxo-erythromycin-2'-trimethylsilyloxy.

A mixture of 3.08 g of the product of Stage A, 340 mg of imidazole, 32 ml of anhydrous THF and 1.06 ml of hexamethyl-disilylazane was stirred at ambient temperature for 4 days. The reaction medium was then evaporated to dryness and the residue was taken up in a mixture of 60 ml of methylene chloride and 60 ml of a 0.5 M aqueous solution of sodium acid phosphate. The mixture was stirred for 15 minutes followed by decanting, extracting with is methylene chloride, drying and evaporating to dryness to obtain 3.345 g of the desired product.

Stage C: 11-deoxy 10,11-didehydro 3-de[(2,6-dideoxy 3-0-methyl α-L-ribohexopyranosyl) oxy]6-0-methyl 3-oxo erythromycin 2'-trimethylsilyloxy 2α-fluoro. p 1.24 ml of a sodium potassium terbutylate in 0.97M THF was added at −12° C., under an argon atmosphere, to a solution of 668 mg of 11-deoxy-10,11-didehydro-3-de[(2,6-dideoxy-3-0-methyl-α-L-ribohexopyranosyl)-oxy]-6-0-methyl-3-oxo-erythromycin-2'-trimethylsilyloxy and 6.7 ml of anhydrous THF. The mixture was stirred for 5 minutes and 378 mg of N-fluoro-dibenzenesulfonimide were added followed by stirring for 10 minutes at −12° C. The mixture was allowed to return to ambient temperature over 90 minutes. Isolation and purification operations were carried out to obtain 695 mg of the desired product.

Stage D: 11-deoxy-10,11-didehydro-3-de[(2,6-dideoxy-3-C-methyl-3-0-methyl-α-L-ribohexopyranosyl)-oxy]-6-0-methyl-3-oxo-erythromycin-2α-fluoro.

A mixture of 5.476 g of the product of Stage c, 50 ml of THF and 11.2 ml of 1M tetrabutylammonium fluoride in THF was stirred for 3 hours 30 minutes and the solvent was evaporated off. 37 ml of ethyl acetate, 37 ml of water and 7.5 ml of ammonium hydroxide at 20% were added and the mixture was stirred for 10 minutes followed by decanting, extraction with ethyl acetate, drying and filtering. The filtrate was concentrated to dryness and the product was chromatographed on silica eluting with an ammoniated $CH_2Cl_2$—MeOH mixture 99-1, then 98-2, 97-3, 96-4, 95-5 to obtain 2.452 g of the desired product.

Stage E: 11-deoxy 10,11-didehydro 3-de[(2,6-dideoxy 3-C-methyl-3-O-methyl-α-L-ribohexopyrasonyl)oxy]6-O-methyl 3-oxo erythromycin 2'-acetoxy 2α-fluoro.

1.02 g of the product of Stage D, 10 ml of methylene chloride and 241 μl of acetic anhydride were stirred for 3 hours followed by evaporation. Then, 10 ml of water and 10 ml of ethyl acetate were added and the reaction medium stood for 1 hour at ambient temperature with stirring, followed by decanting, drying and evaporating to obtain 1.01 g of the desired product.

Stage F: 12-(oxycarbonylimidazol)-11-deoxy-10,11-didehydro-3-de[(2,6-dideoxy-3-C-methyl-3-0-methyl-α-L-ribohexopyranosyl)-oxy]-6-0-methyl-3-oxo-erythromycin-2'-acetoxy-2α-fluoro.

0.388 g of carbonyldiimidazole and 24 μl of DBU were added at 0° C. to a solution of 1.01 g of the product of Stage E and 10 ml of anhydrous THF and the mixture was stirred at 0° C. for 19 hours. The THF was evaporated off and 10 ml of water and 10 ml of ethyl acetate were added. The reaction mixture was stirred for 10 minutes followed by extracting, drying and evaporating to obtain 0.902 g of the crude sought product which was chromatographed eluting with an ethyl acetate-triethylamine mixture 96-4 to obtain 0.573 g of the desired product.

EXAMPLE 3

(3aS,4R,7S,9R,10R,11R,13R,15R,15aR,18S)-4-ethyl-7-fluoro-3a,4,10,11,12,13,15,15a-octahydro-18-[[[(4-quinoleinyl)carbonyl]oxy]methyl]-11-methoxy-3a,7,9,11,13,15-hexamethyl-10-[[3,4,6-trideoxy-3-(dimethylamino)-.beta. -D-xylo-hexopyranosyl]oxy]-14,1-(nitriloethano)-2H-oxacyclotetradecino[4,3-d]oxazole-2,6,8(7H,9H)-trione Stage A: (3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[2-O-acetyl-3,4,6-trideoxy-3-(dimethylamino)-.beta.-D-xylo-hexopyranosyl]oxy]-14,1-(nitriloethano)-2H-oxacyclotetradecino[4,3-d]oxazole-2,6,8(7H,9H)-trione 299 mg of the product of Example 2, 3 ml of ethyl acetate and 46 µl of acetic anhydride were stirred at ambient temperature for 20 hours and then was poured into a 20% saturated solution of ammonium hydroxide followed by stirring for 20 minutes, decanting and extracting with ethyl acetate, drying, filtering and evaporating to obtain 0.3296 g of the desired product.

Stage B:(3aS,4R,7S,9R,10R,11R,13R,15R,15aR,18S)-4-ethyl-7-fluoro-3a,4,10,11,12,13,15,15a-octahydro-18-[[[(4-quinoleinyl)carbonyl]oxy]methyl]-11-methoxy-3a,7,9,11,13,15-hexamethyl-10-[[2-O-acetyl-3,4,6-trideoxy-3-(dimethylamino)-.beta.-D-xylo-hexopyranosyl]oxy]-14,1-(nitriloethano)-2H-oxacyclotetradecino[4,3-d]oxazole-2,6,8(7H,9H)-trione A mixture of 180 mg of the product of Stage A, 6 ml of methylene chloride, 137 µl of TEA, 0.142 g of acid chloride and 33.2 mg of DMAP was refluxed for 5 hours 30 minutes and the reaction mixture was then poured into a 10% aqueous solution of ammonium hydroxide followed by decanting. The organic phase was washed with a saturated aqueous solution of sodium chloride and the aqueous phase was extracted with ethyl acetate. The organic phases were combined, dried, filtered and evaporated to obtain 0.23 g of the crude sought product which was purified by chromatography on silica eluting with a chloroform, isopropyl alcohol, ammonium hydroxide mixture 96-4-0,1%.

Stage C: (3aS,4R,7S,9R,10R,11R,13R,15R,15aR,18S)-4-ethyl-7-fluoro-3a,4,10,11,12,13,15,15a-octahydro-18-[[[(4-quinoleinyl)carbonyl]oxy]methyl]-11-methoxy-3a,7,9,11,13,15-hexamethyl-10-[[3,4,6-trideoxy-3-(dimethylamino)-.beta. -D-xylo-hexopyranosyl]oxy]-14,1-(nitriloethano)-2H-oxacyclotetradecino[4,3-d]oxazole-2,6,8(7H,9H)-trione.

A mixture of 0.135 g of the product of Stage B and 2 ml of methanol was stirred for 24 hours followed by evaporating to dryness. The residue was taken up in ethyl acetate and 20 ml of 10% ammonium hydroxide were added. The mixture was stirred for 10 minutes followed by decanting, extracting with ethyl acetate, drying, filtering and evaporating. The residue was taken up in ether, filtered and dried to obtain the desired product with a rf=0.40 (CHCl$_3$, MeOH, NH$_4$OH=96-4-0.4, and with a mass spectrum MH$^+$=683$^+$.

Example of Pharmaceutical Composition

Tablets containing 150 mg of the Product of Example 1 and sufficient excipient of starch, talc, magnesium stearate for 1 g tablets.

PHARMACOLOGICAL STUDY

Method of Dilutions in Liquid Medium

A series of tubes were prepared in which the same quantity of nutritive sterile medium was distributed. Increasing quantities of the product to be studied were distributed into each tube and then each tube was seeded with a bacterial strain. After incubation for twenty-four hours in an oven at 37° C., the growth inhibition was evaluated by transillumination, which allowed the minimal inhibitory concentrations (M.I.C.) to be determined, expressed in micrograms/ml. The following results were obtained: (reading after 24 hours)

| GRAM$^+$ bacterial strains | Example 1 | Example 3 |
|---|---|---|
| S. aureus 011UC4 | 0.150 | 0.040 |
| S. aureus 011UC4 + 50% serum | 0.040 | 0.040 |
| S. aureus 011GO25I | 0.600 | 0.040 |
| S. epidermidis 012GO11I | 0.300 | 0.150 |
| S. pyogenes 02A1UC1 | 0.040 | # 0.02 |
| S. agalactiae 02B1HT1 | # 0.02 | 0.02 |
| S. faecalis 02D2UC1 | 0.040 | 0.02 |
| S. faecium 02D3HT1 | # 0.02 | 0.02 |
| Streptococcus gr. G 02GOGR5 | 0.040 | 0.02 |
| S. mitis 02MitCB1 | 0.040 | 0.02 |
| S. agalactiae 02B1SJ1c | 1.200 | 0.02 |
| S. pneumoniae 032UC1 | 0.080 | 0.02 |
| S. pneumoniae 030GR20 | # 0.02 | 0.02 |

Moreover, the product of Example 1 showed a useful activity on the following Gram bacterial strains: Haemophilus Influenzae 351HT3, 351CB12 and 351CA1.

Various modifications of the products of the invention may be made without departing from the spirit or scope thereof and it is to be understood that the invention is intended to be limited only as defined in the appended claims.

What we claim is:

1. A compound selected from the group consisting of the formula

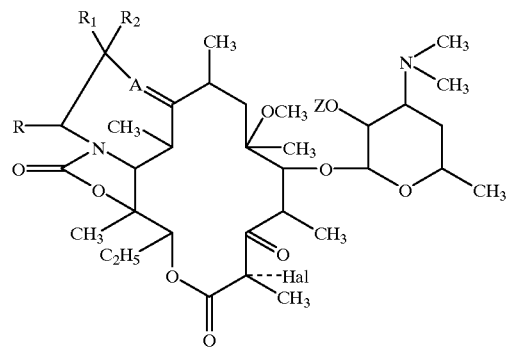

I wherein A is nitrogen or N→O, $R_1$ and $R_2$ are individually selected from the group consisting of hydrogen and alkyl of 1 to 18 carbon atoms, R is —(CH$_2$)$_m$OB, Hal is halogen, m and n are individually an integer from 1 to 8, B is hydrogen or

or —(CH$_2$)$_n$—Ar, Ar is a mono- or polycyclic aryl or heteroaryl, Z is hydrogen or acyl of an organic carboxylic acid of up to 18 carbon atoms and its non-toxic, pharmaceutically acceptable acid addition salts.

2. A compound of claim 1 wherein R$_1$ and R$_2$ are hydrogen.

3. A compound of claim 1 wherein A is nitrogen.

4. A compound of claim 1 wherein Hal is fluorine.

5. A compound of claim 1 wherein R is —CH$_2$OH.

6. A compound of claim 1 which is (3aS, 4R*, 7S*, 9R*,10R*, 11R*, 13R*, 15R*, 15aR*, 18S*)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-.beta.-D-xylo-hexopyranosyl]oxy]-14,1-(nitriloethano)-2H-oxacyclotetradecino[4,3-d]oxazole-2,6,8(7H,9H)-trione.

7. An antibiotic composition comprising an antibiotically effective amount of a compound of claim 1 and an inert pharmaceutical carrier.

8. An antibiotic composition comprising an antibiotically effective amount of a compound of claim 6 and an inert pharmaceutical carrier.

9. A method of treating bacterial infections in warm-blooded animals comprising administering to warm-blooded animals in need thereof an antibiotically effective amount of a compound of claim 1.

10. A method of treating bacterial infections in warm-blooded animals comprising administering to warm-blooded animals in need thereof an antibiotically effective amount of a compound of claim 6.

11. A process for the preparation of a compound of claim 1 comprising reacting a compound of the formula

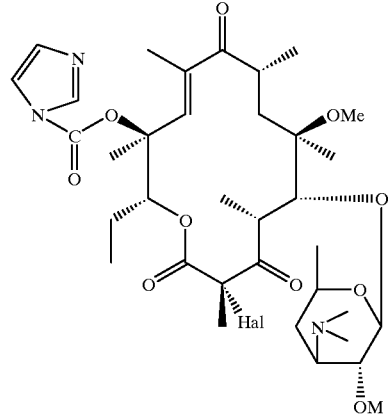

wherein Hal is halogen and OM is a protected hydroxyl with a compound of the formula

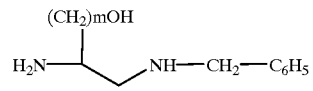

wherein m is an integer from 1 to 8 to obtain a compound of the formula

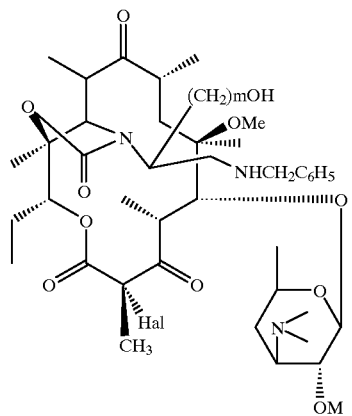

deprotecting the 2'-hydroxyl to obtain a compound of the formula

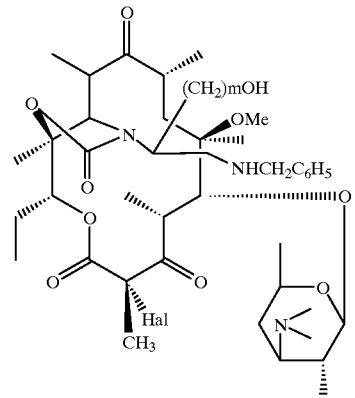

reacting the latter with a debenzylating agent to obtain a compound of the formula

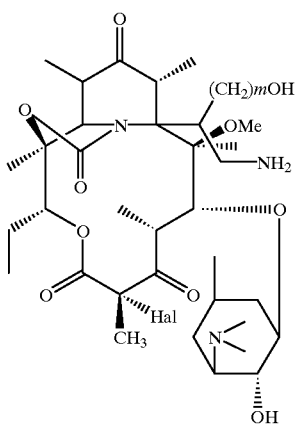

VI

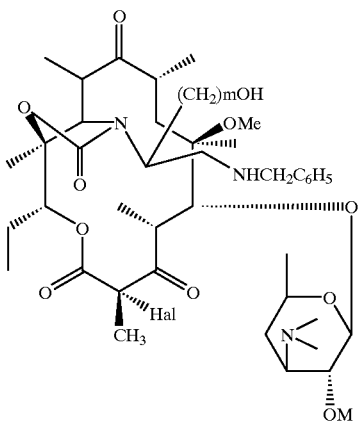

IV reacting the latter with a cyclization agent to form a compound of the formula

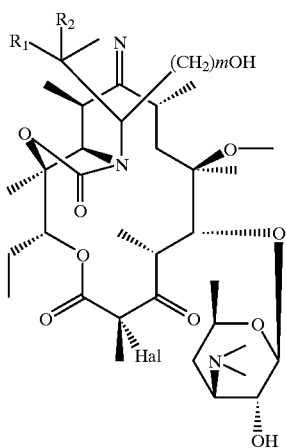

IA corresponding to a compound of Formula I of claim 1 wherein R is —(CH$_2$)$_m$—OH and optionally subjecting the latter to an aralkylating or acylating agent to obtain a compound of Formula I of claim 1 wherein B is —(CH$_2$)$_n$—Ar or

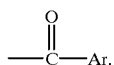

12. A compound selected from the group consisting of

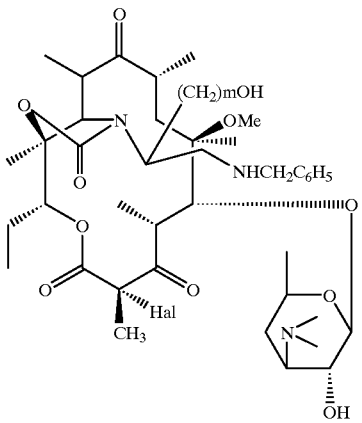

V

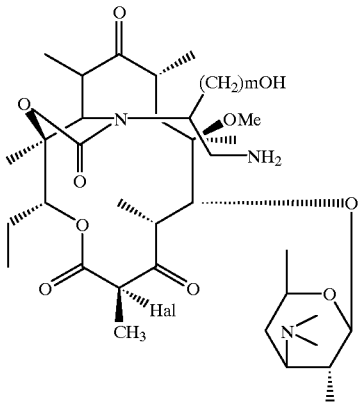

VI

[VI structure repeated]

where the substituents are defined as in claim 11.

* * * * *